US010433843B2

(12) United States Patent
Yee

(10) Patent No.: US 10,433,843 B2
(45) Date of Patent: Oct. 8, 2019

(54) WEDGE ASSEMBLY FOR SURGICAL STAPLE CARTRIDGE

(71) Applicant: AESCULAP AG, Tuttlingen (DE)

(72) Inventor: Kristopher J. Yee, San Jose, CA (US)

(73) Assignee: Aesculap AG (DE)

( * ) Notice: Subject to any disclaimer, the term of this patent is extended or adjusted under 35 U.S.C. 154(b) by 243 days.

(21) Appl. No.: 15/640,301

(22) Filed: Jun. 30, 2017

(65) Prior Publication Data
US 2019/0000480 A1    Jan. 3, 2019

(51) Int. Cl.
A61B 17/072    (2006.01)
A61B 17/064    (2006.01)
A61B 90/00     (2016.01)

(52) U.S. Cl.
CPC .... *A61B 17/07207* (2013.01); *A61B 17/0644* (2013.01); *A61B 2017/07228* (2013.01); *A61B 2017/07257* (2013.01); *A61B 2017/07271* (2013.01); *A61B 2017/07278* (2013.01); *A61B 2017/07285* (2013.01); *A61B 2090/037* (2016.02)

(58) Field of Classification Search
CPC ........ A61B 17/07207; A61B 2090/037; A61B 17/0644; A61B 2017/07285; A61B 2017/07271; A61B 2017/07257; A61B 2017/07228; A61B 2017/07278
See application file for complete search history.

(56) References Cited

U.S. PATENT DOCUMENTS

| 5,941,442 | A  | * | 8/1999  | Geiste      | A61B 17/07207 227/175.1 |
| 7,635,074 | B2 | * | 12/2009 | Olson       | A61B 17/07207 227/176.1 |
| 7,641,091 | B2 | * | 1/2010  | Olson       | A61B 17/07207 227/175.1 |
| 7,669,746 | B2 | * | 3/2010  | Shelton, IV | A61B 17/07207 227/175.1 |
| 7,988,026 | B2 |   | 8/2011  | Knodel et al. | |
| 8,127,976 | B2 | * | 3/2012  | Scirica     | A61B 17/07207 227/176.1 |
| 8,261,958 | B1 | * | 9/2012  | Knodel      | A61B 17/064 227/176.1 |
| 8,276,594 | B2 | * | 10/2012 | Shah        | A61B 17/07207 128/898 |
| 8,365,973 | B1 | * | 2/2013  | White       | A61B 17/0644 227/176.1 |

(Continued)

Primary Examiner — Julian W Woo
(74) Attorney, Agent, or Firm — RatnerPrestia

(57) ABSTRACT

A surgical apparatus includes a cartridge; a staple strip; and staples affixed to the staple strip. Each staple is affixed to the staple strip at a joint. The staples on each staple strip are arranged in rows. The staples in adjacent rows are staggered. A wedge assembly includes a plurality of wedges spaced from one another, each wedge including a shear bump on its upper surface. Each shear bump has a first length. The shear bumps are aligned with one another within a distance equal to the first length. The wedge assembly is slidable relative to the staples to cause at least one wedge to make contact with one of the staples to rotate the staple about the joint, and then break the staple from the joint with the staple strip upon contact between the at least one of the staples and the shear bump of the wedge.

20 Claims, 3 Drawing Sheets

(56) References Cited

U.S. PATENT DOCUMENTS

| | | | | |
|---|---|---|---|---|
| 8,464,922 | B2* | 6/2013 | Marczyk | A61B 17/0644 227/176.1 |
| 8,631,990 | B1* | 1/2014 | Park | A61B 17/0644 227/175.2 |
| 8,789,739 | B2* | 7/2014 | Swensgard | A61B 17/07207 227/177.1 |
| 8,893,950 | B2* | 11/2014 | Marczyk | A61B 17/07207 227/175.1 |
| 9,004,339 | B1 | 4/2015 | Park | |
| 9,016,539 | B2* | 4/2015 | Kostrzewski | A61B 17/07207 227/175.1 |
| 9,113,870 | B2* | 8/2015 | Viola | A61B 17/0644 |
| 9,307,986 | B2* | 4/2016 | Hall | A61B 17/068 |
| 9,629,628 | B2* | 4/2017 | Aranyi | A61B 17/07207 |
| 9,757,130 | B2* | 9/2017 | Shelton, IV | A61B 17/07207 |
| 9,788,835 | B2* | 10/2017 | Morgan | A61B 17/0644 |
| 9,855,042 | B1* | 1/2018 | Kang | A61B 17/07207 |
| 9,867,616 | B2* | 1/2018 | Marczyk | A61B 17/0644 |
| 2017/0303923 | A1* | 10/2017 | Scheib | A61B 17/068 |

\* cited by examiner

WEDGE ASSEMBLY FOR SURGICAL STAPLE CARTRIDGE

FIELD OF THE INVENTION

The invention generally relates to surgical staplers and stapling.

BACKGROUND

A surgical stapler both staples and cuts tissue to transect that tissue while leaving the cut ends hemostatic. A typical surgical stapler receives at its distal end a disposable single-use cartridge with several rows of staples, and includes an anvil opposed to the cartridge.

Surgical staplers generally are configured to receive surgical staple cartridges so that one tool can be used with multiple cartridges in a surgical procedure. Conventional surgical staplers utilize cartridges with six longitudinal rows of staples, three on either side of a knife. Further, conventional surgical staple cartridges interpose a staple driver between each staple and a wedge; the wedge moves longitudinally and serially contacts the staple drivers, which translate the longitudinal motion of the wedge into motion of the corresponding staples in a second, perpendicular direction toward an anvil. Surgical stapler cartridges manufactured by Dextera Surgical Inc. of Redwood City, Calif. instead utilize four longitudinal rows of staples, two on either side of a knife. Such surgical stapler cartridges further do not utilize staple drivers; instead, the wedge serially contacts staples that are frangibly affixed to a strip, rotates each staple about its point of affixation to the strip to close the staple, and shears each staple from the strip, such as described in commonly-assigned U.S. Pat. No. 7,988,026, which is incorporated by reference herein in its entirety.

Staples in a cartridge typically are arranged in rows that are staggered relative to one another. This staggered arrangement promotes hemostasis in treated tissue, by closing off straight channels through which blood might flow between closed staples. During actuation, typically one staple in each row is formed simultaneously during longitudinal travel of the wedge. However, by forming one staple in each row simultaneously, the forces required to deploy each of those staples are combined. In a conventional manual, non-powered surgical stapler, that requires the user to input a larger force in order to translate the wedge and actuate the stapler. As the force required increases for a particular tool, the number of users capable of actuating the tool decreases.

BRIEF DESCRIPTION OF THE DRAWINGS

The use of the same reference symbols in different figures indicates similar or identical items.

DETAILED DESCRIPTION

Structure

Figure 1:
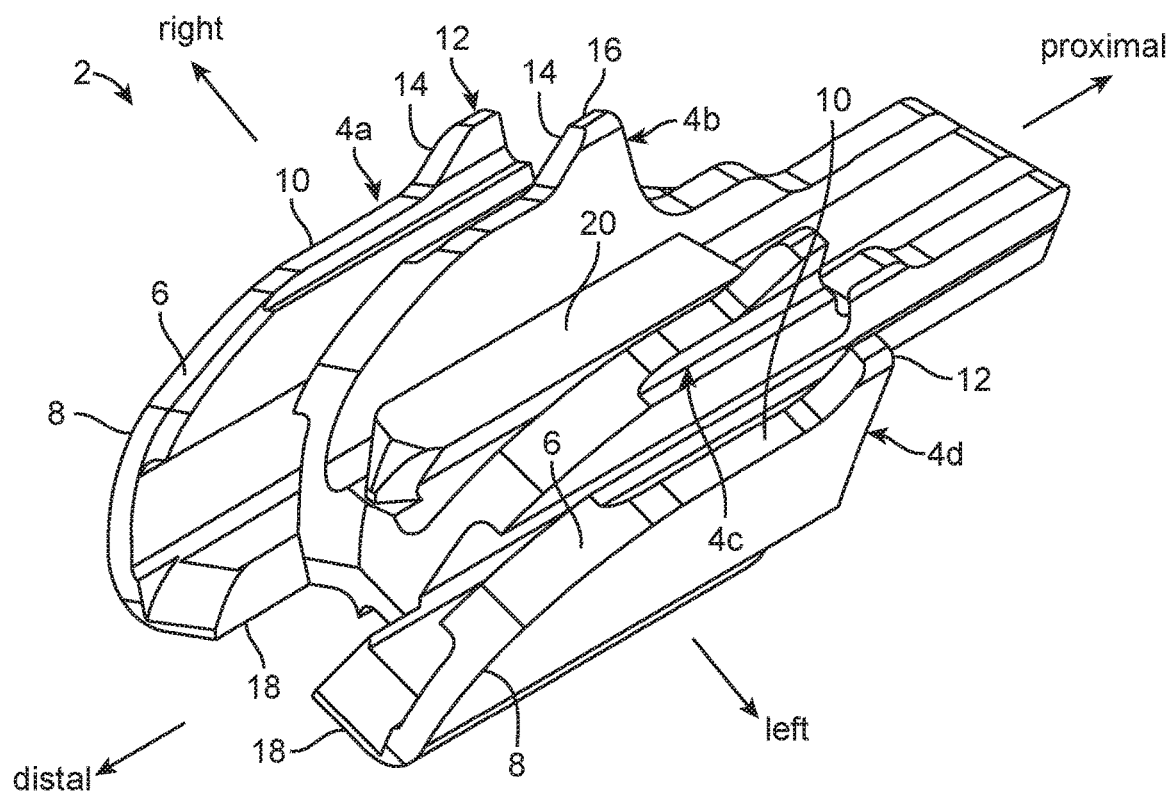
FIG. 1 is a perspective view of an exemplary wedge assembly.

Referring to FIG. 1, a wedge assembly 2 is shown. The wedge assembly 2 includes at least one wedge 4. As seen in FIG. 1, the wedge assembly 2 includes four wedges 4a, 4b, 4c, 4d. The wedge assembly 2 may include fewer or more wedges 4. The number of wedges 4 corresponds to the number of rows of staples to be deployed, as described in greater detail below. For clarity, the wedges 4 of the embodiment of the wedge assembly 2 shown in FIG. 1 may be characterized as the right outer wedge 4a, right inner wedge 4b, left inner wedge 4c, and left outer wedge 4d. The inner wedges 4b, 4c are laterally closer to the longitudinal centerline of the wedge assembly 2 than the outer wedges 4a, 4d. The left and right directions are illustrated in FIG. 1 for clarity. The directions of left and right are selected here to correspond to left and right as perceived by a user. Similarly, the proximal and distal directions, as conventionally understood in the art, are identified in FIG. 1.

Each wedge 4 may include an upper surface 6 that includes a nose 8, a plateau 10, and a shear bump 12. The shape of the surface 6 is related to the deployment of staples, as described in greater detail below. The nose 8 may be curved upward in the distal direction, and may be substantially convex. Alternately, the nose 8 may be curved or shaped in any other suitable manner. Distal to the nose 8, the plateau 10 may be substantially planar and substantially flat. The plateau 10 may be substantially parallel to the longitudinal centerline of the wedge assembly 2. As seen in FIG. 1, the plateaus 10 of the lateral-most wedges 4 (here, the right outer wedge 4a and the left outer wedge 4d) may be longer than the plateaus 10 of the inner wedges 4b, 4c. As described in greater detail below, this difference in length between the plateaus 10 of the lateral-most wedges 4a, 4d and the remaining wedges 4b, 4c causes greater force to be applied to staples 42 in the outer rows than to staples 42 in the inner rows, and also causes the staples 42 in the outer rows to deploy at a different time than staples 42 in the inner rows.

Proximal to the plateau 10, the shear bump 12 is higher than the plateau 10. The shear bump 12 may be positioned at the proximal end of the upper surface 6 of the corresponding wedge 4. Alternately, the shear bump 12 may be spaced distally from the proximal end of the corresponding wedge 4. The shear bump 12 may include a ramp 14 that extends upward in the proximal direction from the plateau 10. The ramp 14 may be generally planar, or may be curved or shaped in any other suitable manner. Proximal to the ramp 14, the shear bump 12 may include a bump plateau 16 that may be substantially planar and substantially flat. In some embodiments, the bump plateau 16 may be substantially parallel to the plateau 10 and thus parallel to the longitudinal axis of the wedge assembly 2.

Figure 2:
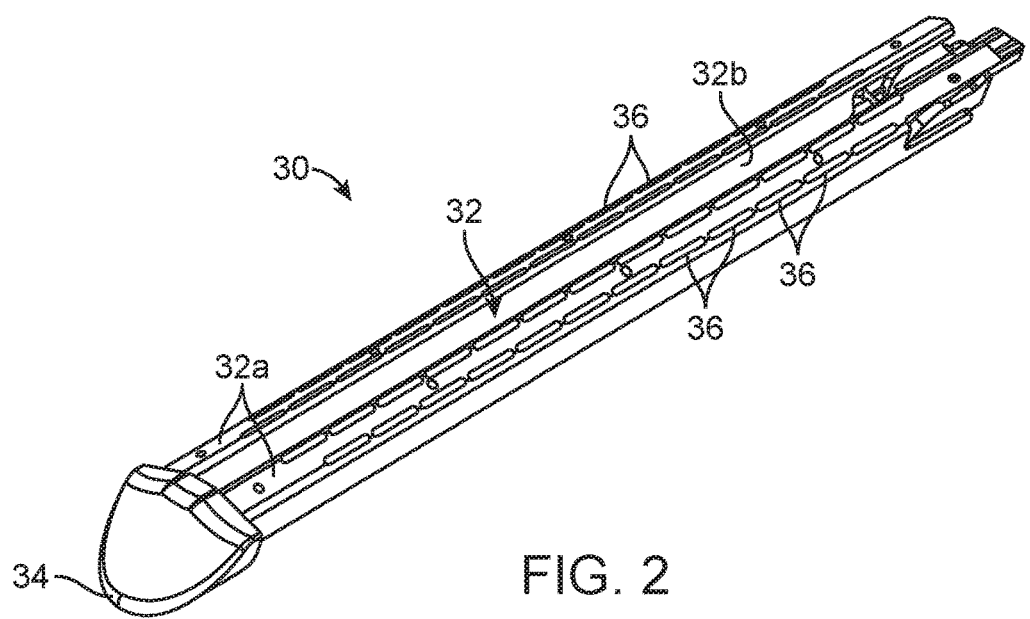
FIG. 2 is a perspective view of an exemplary surgical staple cartridge with the wedge assembly of FIG. 1 in an initial pre-deployment position.

The wedges 4 are spaced laterally apart from one another. The wedges 4 may be angled relative to the longitudinal centerline of the wedge assembly 2 such that the shear bumps on the lateral-most wedges 4 (here, the right outer wedge 4a and the left outer wedge 4d) are spaced laterally apart a distance greater than the distance between the lower edges 18 of the lateral-most wedges 4. Referring also to FIG. 2, the angle between the wedges 4 and the longitudinal centerline of the wedge assembly 2 may be selected such that the bump plateau 16 of each wedge 4 is substantially parallel to the upper surface 32 of the cartridge 30 through which the wedge 4 is slidable.

In some embodiments, each of the shear bumps 12 has substantially the same length. As used in this document, the term "length" refers to a measurement along the longitudinal axis (i.e., the axis along which the proximal and distal directions are defined). Correspondingly, each bump plateau 16 may have substantially the same length. Referring to FIG. 1, the shear bumps 12 may be longitudinally aligned with one another, within a distance equal to the length of a shear bump 12. That is, each shear bump 12 is positioned at a location in the longitudinal direction that is less than or equal to the position of the other shear bumps 12. Any reference point on the shear bumps 12 may be utilized for measuring this alignment, as long as the same reference point is used for each shear bump 12 (e.g., the proximal end of the bump plateau 16). According to some embodiments, the shear bumps 12 may be aligned more closely, within a selected length less than the length of a shear bump 12. According to other embodiments, at least one shear bump 12 has a different length and/or shape that at least one other shear bump 12.

The wedge assembly 2 may include a knife platform 20 from which a knife (not shown) may extend in some embodiments. In this way, as the wedge assembly 2 moves distally to deploy staples, the knife cuts tissue between sets of staples. The knife platform 20 may be positioned substantially at the lateral center of the wedge assembly 2.

Figure 3:
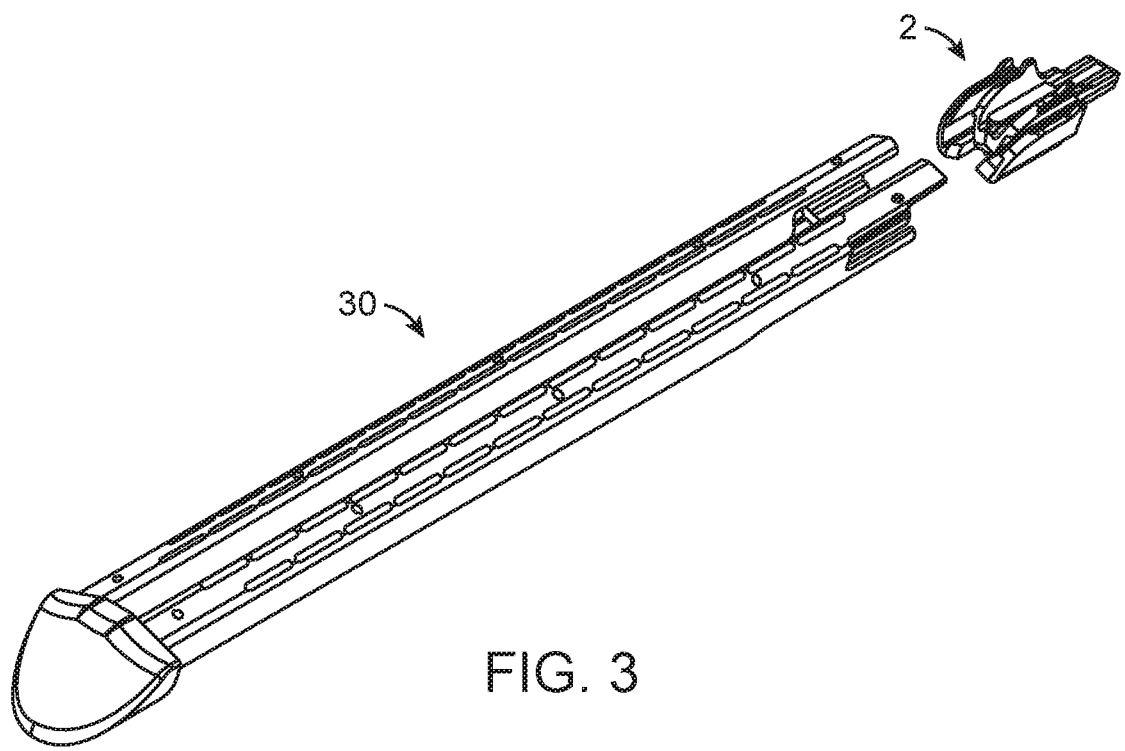
FIG. 3 is an exploded view of FIG. 2, showing the wedge assembly of FIG. 1 spaced apart from and aligned with the surgical staple cartridge.

Referring also to FIG. 2, the wedge assembly 2 is shown in an initial position relative to a cartridge 30. For clarity, FIG. 3 shows the wedge assembly moved proximally away from its initial position relative to the cartridge 30. The wedge assembly 2 is initially in a proximal position relative to the cartridge 30 and moves distally to deploy staples, as described in greater detail below. According to other embodiments, the wedge assembly 2 is initially in a distal position relative to the cartridge 30 and moves proximally to deploy staples. The cartridge 30 includes an upper surface 32. The upper surface 32 may include two lateral sides 32a. The upper surface 32 also may include a centerpiece 32b that separates the two lateral sides 32a. The centerpiece 32b may be planar and substantially horizontal. Each lateral side 32a may be planar, and may angle downward away from its junction with the centerpiece 32b. Each lateral side 32a may angle downward away from its junction with the centerpiece 32b by substantially the same angle. Alternately, one lateral side 32a may angle downward away from its junction with the centerpiece 32b by a different angle than the other. In other embodiments, the upper surface 32 may have any other suitable shape. For example, the entire upper surface 32 may be planar and substantially horizontal; the upper surface 32 may include additional lateral sides 32a; and/or the upper surface 32 may be curved in whole or in part.

Figure 5:
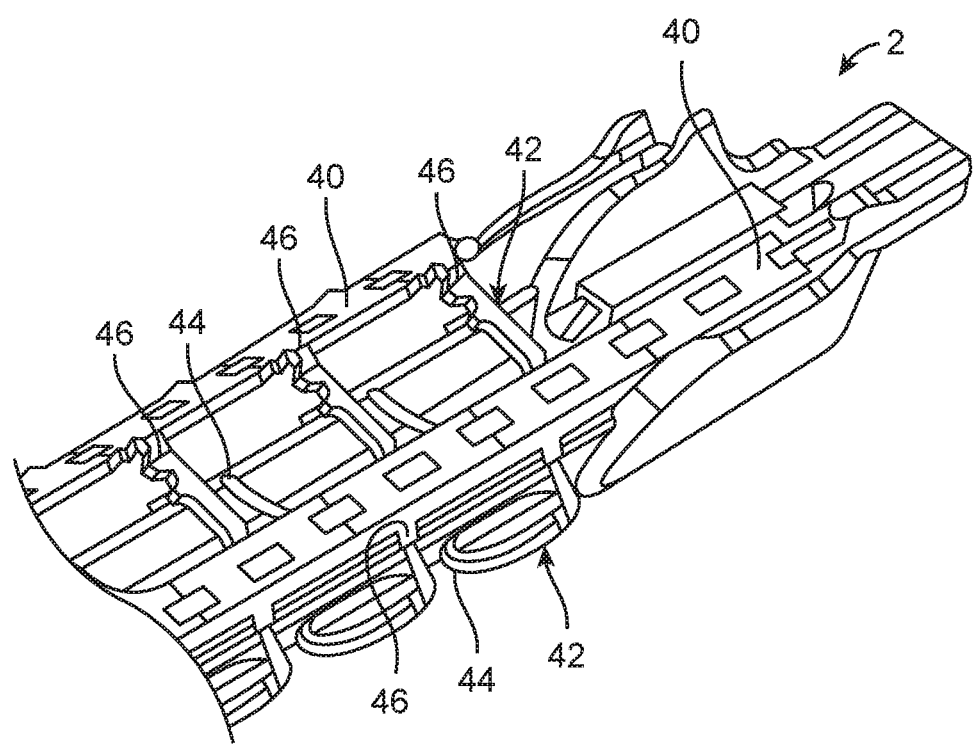
FIG. 5 is a detail view of the proximal end of the exemplary surgical staple cartridge as shown in FIG. 2.

The cartridge 30 includes a tip 34 that may be straight (as shown) or that may be curved for ease of tissue dissection. The upper surface 32 of the cartridge 30 includes a plurality of apertures 36 defined therein. Referring also to FIG. 5, the positions of the apertures 36 correspond to the positions of the staples 42 within the cartridge 30, because the apertures 36 provide openings for the staples 42 to be deployed out of the cartridge 30 into tissue.

Figure 4:
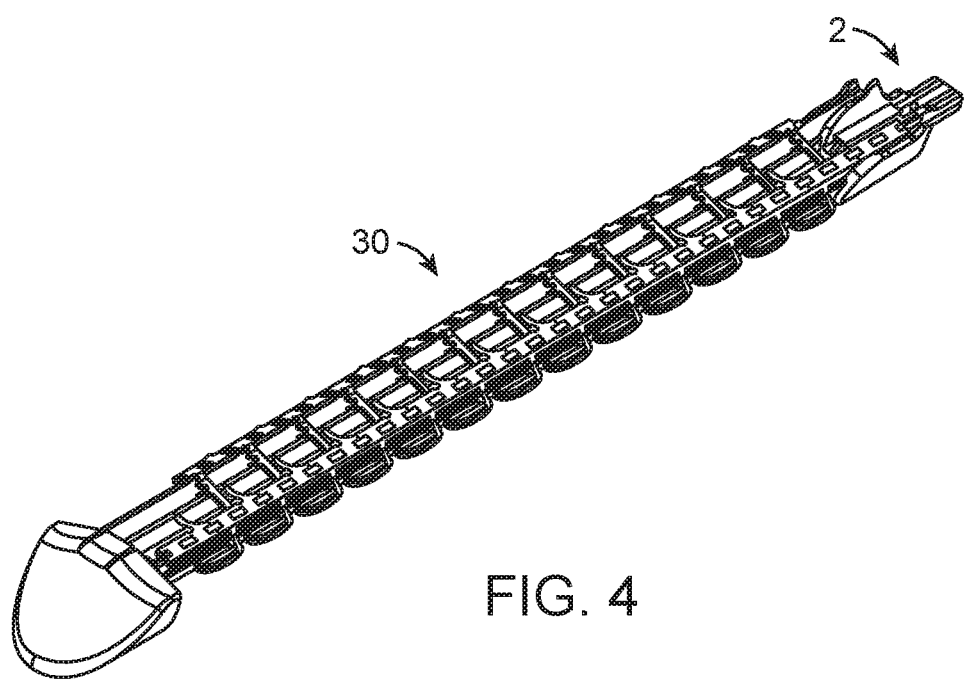
FIG. 4 is a perspective view of the exemplary surgical staple cartridge of FIG. 2, with the cap of the surgical staple cartridge removed.

FIGS. 4-5 show the wedge assembly 2 in an initial position relative to staples 42 in the cartridge 30. The staples 42 are fixed to a staple strip 40 at only a single end 46; the other end 44 is free. The junction between the fixed end 46 of each staple 42 and the staple strip 40 forms a frangible connection therebetween. The staple strip 40 and staples 42 may be configured substantially as described in commonly-assigned U.S. Pat. No. 7,988,026, which is incorporated by reference herein in its entirety.

Each staple strip 40 has two lateral edges, and each staple strip 40 may have a row of staples 42 extending from each of its two lateral edges. The fixed ends 46 of the staples 42 in one row may extend from longitudinal positions along the staple strip 40 that are longitudinally offset from the fixed ends 46 of the staples 42 in the other row extending from the staple strip 40, such that no staple 42 extends from the same longitudinal location on the staple strip 40 as another staple 42. This arrangement of staples 42 along a staple strip 40 is referred to as a "staggered" arrangement of staples 42, such that staples 42 in adjacent rows extending from a staple strip 40 are staggered relative to one another. Such staggering of the staples 42 promotes hemostasis in tissue into which the staples 42 are deployed. Because the positions of the apertures 36 correspond to the positions of the staples 42 in the cartridge 30, the apertures 36 on each lateral side of the cartridge 30 are staggered relative to one another in the same manner as the corresponding staples 42. As seen in FIGS. 2-5, two rows of staples 42 are provided on each lateral side of the cartridge 30, such that the staples 42 are arranged in four longitudinally-extending rows in the cartridge 30, and the staples 42 and corresponding apertures 36 on each individual lateral side are staggered. According to other embodiments, the staples 42 and corresponding apertures 36 may be staggered relative to one another laterally across the entire upper surface 32 of the cartridge 30. In other embodiments, more than two rows of staples 42 are provided on each lateral side of the cartridge 30, and adjacent rows of staples 42 and corresponding apertures 36 on each individual lateral side are staggered relative to one another. For example, staples 42 may be arranged in six longitudinally-extending rows in the cartridge 30, and adjacent rows of staples 42 and corresponding apertures 36 on each individual lateral side are staggered relative to one another.

According to some embodiments, the cartridge 30 is detachably held by a receiver, which is part of an end effector of a surgical stapler. The end effector includes an anvil opposed to the receiver. At least one of the anvil and receiver is rotatable relative to the other in order to clamp tissue with the end effector and release tissue from the end effector. Such a receiver, anvil, end effector and surgical stapler is described in commonly-assigned U.S. Pat. No. 9,004,339, which is incorporated by reference herein in its entirety. According to other embodiments, the cartridge 30 is permanently fixed to and/or nondetachable from the receiver or the end effector. According to other embodiments, the cartridge 30 is not used, and the wedge assembly 2 is slidable through a fixed structure in the end effector of a single-use surgical stapler, where the staples 42 are held in that fixed structure.

Operation

A fresh cartridge 30 is ready for deployment, as seen in FIG. 2. To begin deployment of the staples 42, the wedge assembly 2 that is initially positioned at the proximal end of the cartridge 30 is urged distally. According to other embodiments, the wedge assembly 2 is initially positioned at the distal end of the cartridge 30 and is urged proximally. The motion of the wedge assembly 2 may be caused by actuation of one or more controls on a handle of a surgical stapler, such as described in commonly-assigned U.S. Pat. No. 7,988,026.

As the wedge assembly 2 slides distally relative to the cartridge 30, the upper surface 6 of each wedge 4 sequentially and directly contacts one or more of the staples 42 in a single longitudinally-extending row, in a manner that may be similar to that described in commonly-assigned U.S. Pat. No. 7,988,026. First, the nose 8 of a wedge 4 contacts the most-proximal staple 42 in a row. The shape of the nose 8 begins to rotate the staple 42 about the joint at which the fixed end 46 of the staple 42 is affixed to the staple strip 40. The free end 44 of the staple 42 begins to rotate out of the corresponding aperture 36 in the upper surface 32 of the cartridge 30. As the wedge 4 continues to slide distally, the nose 8 moves distally out of engagement with the staple 42, and the plateau 10 engages the staple 42. Engagement between the plateau 10 and the staple 42 along the length of the plateau 10 causes the staple 42 to continue to rotate about the joint at which the fixed end 46 of the staple 42 is affixed to the staple strip 40, and causes the free end 44 of the staple 42 to continue to rotate out of the corresponding aperture 36 in the upper surface 32 of the cartridge 30. Contact between the plateau 10 and the staple 42 exerts a force on the staple 42. The total force exerted on the staple 42 by the plateau 10 over time is directly proportional to the length of the plateau 10—the longer the plateau 10, the greater the force exerted on the staple 42, and the shorter the plateau 10, the lesser the force exerted on the staple 42.

When the wedge 4 has moved distally such that the staple 42 contacts the proximal end of the plateau 10, rotation of the staple 42 about the joint at which the fixed end 46 of the staple 42 is affixed to the staple strip 40 is substantially complete, such that formation of the staple 42 is substantially complete. The wedge 4 continues its distal motion, and the shear bump 12 then engages the staple 42. Engagement between the shear bump 12 and the staple 42 shears and/or otherwise breaks the staple 42 from the staple strip. For example, as the ramp 14 of the shear bump 12 begins to engage the staple 42, the shear bump 42 begins to push the staple 42 upward relative to the staple strip 40. The substantially completed rotation of the staple 42 about the joint at which the fixed end 46 of the staple 42 is affixed to the staple strip 40 work-hardened the joint, such that the joint is more susceptible to fracture upon the application of shear force thereto. If engagement between the ramp 14 and the staple 42 does not shear or otherwise break the staple 42 from the staple strip 40, then the bump plateau 16 next engages the staple 42 during the continued distal motion of the wedge 4, and then shears or otherwise breaks the staple 42 from the staple strip 40. The wedge 4 continues to move distally, and engages the next most distal staple 42 in the row in the manner described earlier in this paragraph. As the wedge 4 continues to move distally, it sequentially engages some or all of the remaining staples 42 in the row.

Each wedge 4 sequentially engages the staples 42 in a row, substantially in the same manner as described in the previous paragraph. The inner wedges 4b, 4c engage the inner rows of staples 42, and the outer wedge 4a, 4d engage the outer rows of staples. As described above, staples 42 in adjacent rows extending from a staple strip 40 are staggered relative to one another. Further, as described above, the shear bumps 12 may be longitudinally aligned with one another, within a distance equal to the length of a shear bump 12. Because the staples 42 are staggered and the shear bumps 12 are longitudinally aligned with one another within a distance equal to the length of a shear bump 12, less than all of the wedges 4 of the wedge assembly 2 engage staples 42 at the same time. A first set of wedges 4 directly contacts a first set of staples 42 to form and then break off those staples 42 from the staple strip 40. The number of staples 42 in that first set is less than the number of rows of staples 42. Next, a second set of wedges 4 directly contacts a second set of staples 42 to form and then break off those staples 42 from the staple strip 40. The number of staples 42 in that second set is less than the number of rows of staples 42. The number of staples 42 in the first set equals the number of staples 42 in the second set. For example, where four rows of staples 42 are included in the cartridge 30, the first set of staples 42 may include two staples and the second set of staples 42 may include two staples. The wedges 4 then may continue to move, and to contact a subsequent first set of staples 42 and subsequent second set of staples 42, until deployment of all of the staples 42 desired to be deployed is complete. According to an exemplary embodiment, the first set of staples 42 may come from the inner rows, and the second set of staples 42 may come from the outer rows. According to other exemplary embodiments, the first set of staples 42 may come from the outer rows, and the second set of staples 42 may come from the inner rows.

Contacting wedges 4 directly against a first set of staples 42 causes those staples 42 to rotate substantially about a first angle. The amount of rotation is proportional to the length of the plateau 10 on each of the wedges 4. In some embodiments, the plateaus 10 on the wedges 4 that contact the first set of staples 42 are shorter than the plateaus 10 on the wedges 4 that contact the second set of staples 42. As set forth above, the inner wedges 4b, 4c have shorter plateaus 10 than the outer wedges 4a, 4d. The inner wedges 4b, 4c contact the first set of staples 42. Consequently, contacting wedges 4 directly against the second set of staples 42 causes those staples 42 to rotate substantially about a second angle that is greater than the first angle. According to other embodiments, the plateaus 10 on the wedges 4 that contact the first set of staples 42 are longer than the plateaus 10 on the wedges 4 that contact the second set of staples 42, such that contacting wedges 4 directly against the second set of staples 42 causes those staples 42 to rotate substantially about a second angle that is less than the first angle.

The length of each plateau 10 is also proportional to the amount of force applied by the wedge 4 to a staple 42; the longer the plateau 10, the more force is applied to the staple 42. In some embodiments, the plateaus 10 on the wedges 4 that contact the first set of staples 42 are shorter than the plateaus 10 on the wedges 4 that contact the second set of staples 42. Consequently, contacting wedges 4 directly against the second set of staples 42 applies a second force to those staples 42 that is greater than a first force applied to the first set of staples 42. According to other embodiments, the plateaus 10 on the wedges 4 that contact the first set of staples 42 are longer than the plateaus 10 on the wedges 4 that contact the second set of staples 42, such that contacting wedges 4 directly against the second set of staples 42 applies a second force to those staples 42 that is less than a first force applied to the first set of staples 42. A wedge 4 with a longer plateau 10 applies more force to a staple 42, over a longer time, than a wedge 4 with a shorter plateau 10. The shear bumps 12 shear off the staples 42 from the staple strip 40 after application of force to the staple 42 from contact with the plateau 10.

The differential lengths of the plateaus 10 also controls the timing of deployment of the staples 42. According to some embodiments, all of the wedges 4 of the wedge assembly 2 engage staples 42 at substantially the same time, and staples 42 contacted by the inner wedges 4b, 4c with the shorter plateaus 10 are deployed before staples contacted by the outer wedges 4a, 4d with the longer plateaus 10. The staples 42 engaged by the wedges 4 with the shorter plateaus 10 finish engagement with the plateaus 10 and are sheared off by the shear bumps 12 at a time when the staples 42 engaged by the wedges 4 with the longer plateaus 10 are still engaged with those longer plateaus 10. In this way, the first two staples 42 in the inner rows are deployed before the first two staples 42 in the outer rows. Further, the staples 42 engaged by the wedges 4 with the longer plateaus 10 contact those plateaus 10 for a longer time than the staples 42 engaged by the wedges 4 with the shorter plateaus 10.

In other embodiments, the longer plateaus 10 may be located on the inner wedges 4b, 4c and the shorter plateaus 10 may be located on the outer wedges 4a, 4d, such that the staples 42 in the outer rows are deployed before the first two staples 42 in the inner rows. In other embodiments, the longer plateaus 10 may be divided across an inner and an outer wedge 4, with the shorter plateaus 10 positioned on the other inner and outer wedge 4. In all of these configurations, the wedge assembly 2 starts deployment of a set of four staples 42 across four rows at substantially the same time, and finishes deployment of two staples 42 while the other two staples 42 in the set are still being deployed.

According to other embodiments, such as where the staples 42 in a row are spaced longitudinally further apart, wedges 4 may apply a first force to a first set of staples 42 while other wedges 4 apply no force to a second set of staples 42, and then wedges 4 apply no force to a first set of staples while other wedges 4 apply force to a second set of staples 42. In such an embodiment, the staples 42 in a row are spaced longitudinally further apart from one another and/or the wedges 4 are shorter.

As used in this document, and as customarily used in the art, the word "substantially" and similar terms of approximation are used to cover manufacturing tolerances, manufacturing variations, and manufacturing imprecision that are inescapable parts of fabricating any mechanism or structure.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. Surgical apparatus, comprising:
a cartridge;
a staple strip held within said cartridge;
a plurality of staples affixed to said staple strip, wherein each said staple is affixed to said staple strip at a single joint, and wherein said staples on each staple strip are arranged in longitudinally-extending rows and said staples in adjacent said rows are staggered relative to one another; and
a wedge assembly including a plurality of wedges laterally spaced from one another, each said wedge including a shear bump on an upper surface thereof and a longitudinally-extending plateau on said upper surface thereof distal to the corresponding said shear bump, wherein at least one said plateau is longer than a remainder of said plateaus;
wherein said wedge assembly is slidable relative to said staples to cause at least one said wedge to make direct contact with at least one of said staples to rotate said at least one said staple about said joint, and then break at least one of said staples from said joint with said staple strip upon contact between said at least one of said staples and said shear bump of said wedge.

2. The surgical apparatus of claim 1, wherein said wedges are angled such that said shear bumps on the lateral-most two said wedges are spaced apart a distance greater than the distance between the lower edges of the lateral-most two said wedges.

3. The surgical apparatus of claim 1, further comprising an end effector comprising an anvil and a channel, wherein said cartridge is detachably receivable in said channel.

4. The surgical apparatus of claim 1, wherein said shear bumps on said wedges are longitudinally aligned with one another within a distance less than said first length.

5. The surgical apparatus of claim 1, wherein said plurality of staples are arranged in four longitudinally-extending rows.

6. The surgical apparatus of claim 1, wherein said plurality of staples are arranged in six longitudinally-extending rows.

7. The surgical apparatus of claim 1, wherein said plateaus of the lateral-most said wedges are longer than said plateaus of the other said wedges.

8. The surgical apparatus of claim 7, wherein said plateaus of said lateral-most said wedges are substantially the same length as one another.

9. The surgical apparatus of claim 1, wherein at least one said shear bump is positioned at a proximal end of an upper surface of at least one said wedge.

10. The surgical apparatus of claim 1, wherein each said shear bump includes a ramp angled upward in the proximal direction, and a bump plateau proximal to said ramp, wherein said bump plateau lies in a plane parallel to the longitudinal axis of said wedge assembly.

11. A method for surgical stapling, comprising:
possessing a surgical stapler, comprising: a staple holder; a plurality of staples positioned within said staple holder, said plurality of staples organized in a plurality of rows; a staple strip to which each of said plurality of staples is fixed; and at least one wedge assembly, wherein said wedge assembly includes a plurality of wedges laterally spaced from one another, each said wedge including a shear bump on an upper surface thereof and a longitudinally-extending plateau on said upper surface thereof distal to the corresponding said shear bump, wherein at least one said plateau is longer than a remainder of said plateaus; and
moving said wedge assembly relative to said staples, wherein said moving comprises
contacting a first set of said wedges directly against a first set of said staples in a first group of rows to form said first set of said staples and then break said first set of staples from said staple strip, said first set of said staples numbering less than the number of said rows, then
contacting a second set of said wedges directly against a second set of said staples in a different, second group of rows to form said second set of said staples and then break said second set of staples from said staple strip after said first set of said staples;
wherein the number of said staples in said first set and the number of said staples in said second set equals said number of said rows.

12. The method of claim 11, further comprising
continuing said moving, and
repeating said contacting said first set of said wedges directly against a first set of said staples and said contacting said second set of said wedges directly against a second set of said staples, until deployment of said staples is complete.

13. The method of claim 11, wherein said first group of said rows is the inner rows and said second group of said rows is the outer rows.

14. The method of claim 11, wherein said first group of said rows is the outer rows and said second group of said rows is the inner rows.

15. The method of claim 11, wherein
said contacting said first set of said wedges directly against a first set of said staples in a first group of rows to form said first set of said staples causes said first set of said staples to bend through a first angle;
said contacting said second set of said wedges directly against a second set of said staples in a different, second group of rows to form said second set of said staples causes said second set of said staples to bend through a second angle; and
said first angle is different from said second angle.

16. The method of claim 15, wherein
said first group of said rows is the inner rows and said second group of said rows is the outer rows; and
said second angle is greater than said first angle.

17. The method of claim 11, wherein
said contacting said first set of said wedges directly against a first set of said staples in a first group of rows to form said first set of said staples applies a first force to each said staple in said first set;
said contacting said second set of said wedges directly against a second set of said staples in a different, second group of rows to form said second set of said staples applies a second force to each said staple in said second set; and
said first force is different from said second force.

18. The method of claim 17, wherein
said first group of said rows is the inner rows and said second group of said rows is the outer rows; and
said second force is greater than said first force.

19. The method of claim 18,
wherein said plateaus of said second set of said wedges are longer than said plateaus of said first set of said wedges; and
wherein said contacting said plateaus of said second set of said wedges directly against said second set of said staples is performed for a longer duration than said contacting said plateaus of said first set of said wedges directly against said first set of said staples.

20. The method of claim 11, wherein said first set of said wedges includes a left inner wedge and a right inner wedge, and said second set of said wedges includes a left outer wedge and a right outer wedge.

* * * * *